United States Patent [19]
Lambert

[11] Patent Number: 5,394,890
[45] Date of Patent: Mar. 7, 1995

[54] INGROWN TOENAIL RELIEF SADDLE

[76] Inventor: William S. Lambert, 52 Tokalon, Metairie, La. 70001

[21] Appl. No.: 728,250

[22] Filed: Jul. 10, 1991

[51] Int. Cl.⁶ .......................... A61F 5/37; A61F 13/08
[52] U.S. Cl. ..................... 128/846; 128/893
[58] Field of Search ............... 128/892, 893, 894, 846; 604/292, 304, 307; 2/21

[56] References Cited

U.S. PATENT DOCUMENTS

| | | | |
|---|---|---|---|
| 2,740,401 | 4/1956 | Crawford | 128/894 |
| 3,388,702 | 6/1968 | Steel | 128/894 |
| 3,616,156 | 10/1971 | Scholl | 128/893 |
| 4,516,571 | 5/1985 | Buchan | 128/893 |
| 4,926,883 | 5/1990 | Strock | 128/892 |
| 5,181,914 | 1/1993 | Zook | 128/893 |

FOREIGN PATENT DOCUMENTS

| | | | |
|---|---|---|---|
| 1114893 | 5/1968 | United Kingdom | 128/894 |
| 1251203 | 10/1971 | United Kingdom | 128/894 |

Primary Examiner—Michael A. Brown

[57] ABSTRACT

A device for reversing growth direction of ingrown toenails is provided with a first flat portion which is adhesively secured to a top surface of a toenail, such that the front outer corners of the first portion are positioned above and immediately adjacent to ingrown toenail corners, and a second, wedge-shaped portion which is integrally attached to the first portion. The inner surfaces of the first and second portions are provided with a plurality of parallel rows of teeth which are angled, so as to allow meshing of the teeth of the first portion and the second portion, while preventing withdrawal of the wedged portion from its engagement with the first portion, when in place. The wedge is gradually pushed between the top surface of the toenail and the bottom surface of the first portion, causing uplifting of the ingrown toenail corners and relief of pressure on surrounding tissue.

9 Claims, 4 Drawing Sheets

5,394,890

INGROWN TOENAIL RELIEF SADDLE

BACKGROUND—FIELD OF THE INVENTION

This invention relates to devices for reversing direction of growth of ingrown toenails, so as to relieve pressure applied by free edge corners of an ingrown toenail on the surrounding tissue.

The problem of ingrown toenails has been long existing and is defined as a condition in which the sharp edge of a nail grows into the flesh of a toe, usually the big toe. The sharp nail edge pierces the surrounding fold of tissue and causes pain, tenderness, redness, swelling and heat in the toe, and if left untreated, causes a severe inflammation. The traditional cures for ingrown toenails involve prescription of antibiotics to fight the infection and, if necessary in extreme cases, surgical removal of the toenail. In less severe cases, the patient is usually advised to soak the toe in warm water, then to wedge a small piece of cotton under the ingrown nail edge and leave it there. Between soaks various antiseptic creams and lotions are usually prescribed. The cotton is often saturated in alcohol/aseptic solution and is secured in place by tape wrapped around the toe.

Such treatment is painful and causes considerable discomfort since the saturated cotton piece has to be changed several times a day.

The present invention contemplates elimination of drawbacks associated with prior art devices and provide an easy-to-use, inexpensive device for reversing the directional growth of an ingrown toenail.

BRIEF SUMMARY OF THE INVENTION

A device adhesively attachable to the top surface of a toenail to utilize incremental wedging to gradually uplift and reverse upwardly the directionally-ingrowing tissue embedment of the nail corner-points.

BRIEF DESCRIPTION OF THE DRAWINGS

FIG. one is a schematic side view illustrating position of a device in accordance with the present invention on a toenail having ingrown corners.

FIG. two is a free end view of the device in accordance with the present invention positioned on a toenail.

Figure 1:
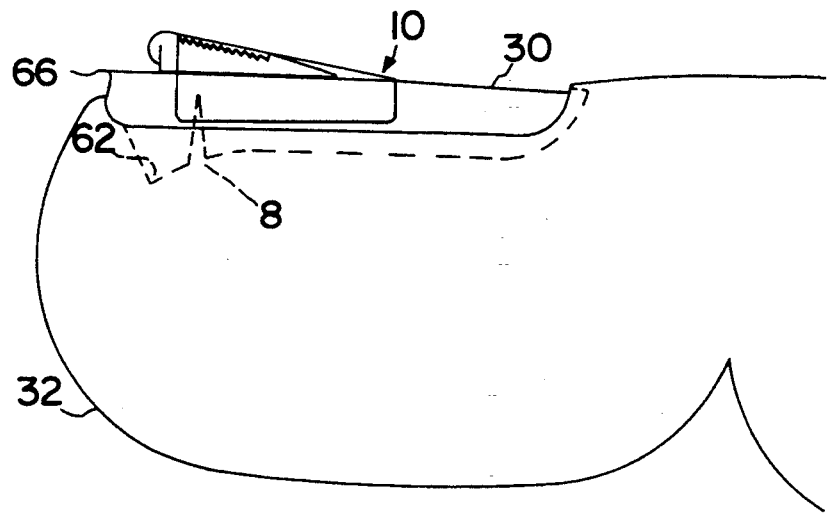

FIG. three is an enlarged view of the device in accordance with present invention, with the shaded area illustrating the area of adhesive coating.

FIG. four is a top view of the device anchored in-place atop toenail.

FIG. five is a frontal view of device anchored in-place atop toenail.

FIG. six is a top view of the device in accordance with the present invention in an unfolded condition.

FIG. seven is a bottom view of the device in accordance with the present invention in an unfolded condition.

FIG. eight depicts sequential views of the employment of the device.

DRAWING REFERENCE NUMERALS 10 device of present invention
12 trapezoidal-shaped first portion of 10
14 wedge-shaped second portion of 10
16 shock-absorbing, wedge-advancing, intermediate portion of 10
18 inner end of 12
20 outer end of 12
22 side of 12 opposing 24
24 side of 12 opposing 22
26 front corner of 12 opposing corner 28
28 front corner of 12 opposing corner 26
30 top of toenail surface of toe 32
32 typical toe illustrating ingrown toenail corner 62
34 is the upper surface of 12
35 is the inner surface of 12
36 rows of teeth formed on the surface of 35
38 root of toenail
40 area of adhesive application to 35 opposite 42
42 area of adhesive application to 35 opposite 40
44 front end of wedge 14
46 inner end of wedge 14
48 top surface of wedge 14
50 toothed bottom surface of wedge 14
52 teeth of 50 complementary to the teeth of 36
54 teeth mesh/alignment 36/50 pressure relief tooth-free areas
56 teeth mesh/alignment 36/50 pressure relief tooth-free areas
60 directional arrow indicating the inward direction of the force of 14
62 ingrown nail corner
64 arrows indicating uplift of nail corners 62
66 free end of toenail 30

DETAILED DESCRIPTION OF THE INVENTION

Referring now to the drawings in detail, FIG. one is a sideview of the subject device 10 adhesively affixed atop the exterior and near the end 66 of the nail 30 of a human toe 32, positioned to actuate an uplifting lateral pulling effect upon the ingrown nail corners 62—suggesting the occasional rupture 8 of the nail. Arrows 64 suggest that effect in the frontal cross-sectional view of FIG. two.

Lateral adherence 40,42 of a first portion 12, in FIG. three, depicts a second portion wedge 14 incrementally insertable per the intermeshed teeth 36/52 shown therein. The top view of these elements of the device in FIG. four indicates the folded buffer portion connecting the first and second portions joined by their intermeshed teeth.

Figure 6:
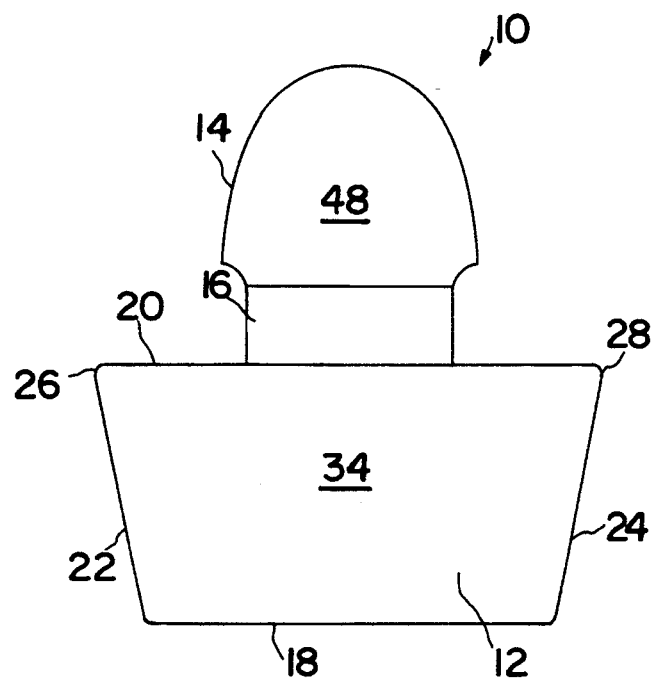
Figure 7:
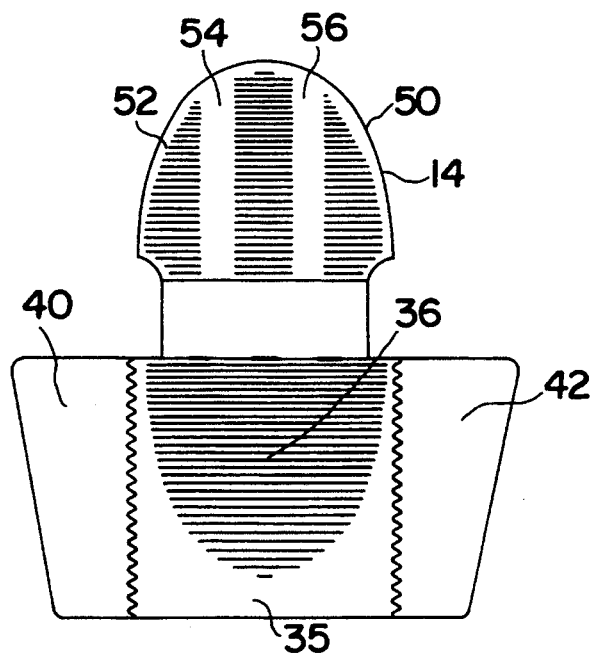

Referring now to the drawings in more detail, and more specifically to FIGS. 6 and 7, the device of the present invention is seen designated by numeral 10. The device 10 comprises a first portion 12, a second portion 14 and an intermediate portion 16, all integrally connected to each other, including a first and second plurality of locking teeth, adapted to intermate and extending from the complementary contractive surfaces of both portions.

Figure 8:
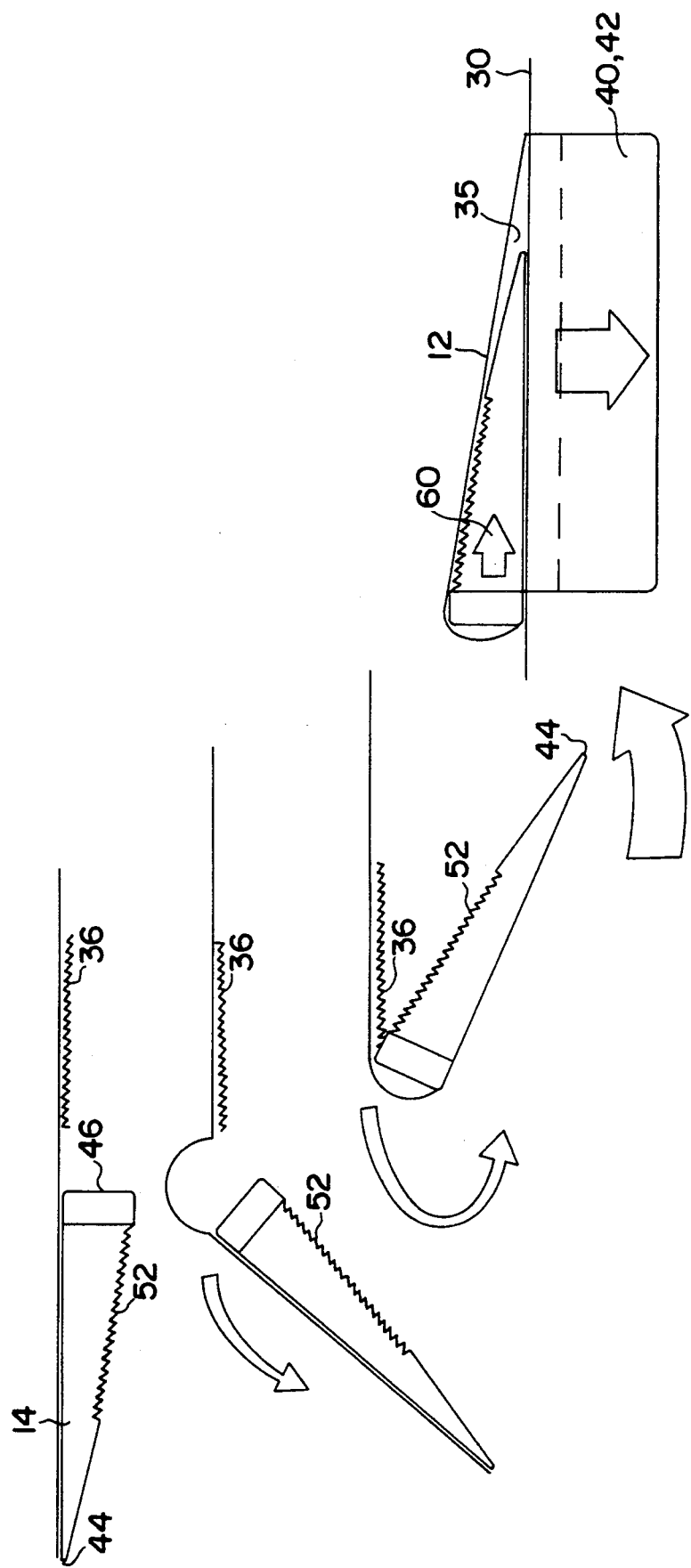

The first portion 12 is sized and shaped in such a manner as to be positioned on a human toenail and span across the toenail from a location adjacent one ingrown toenail corner to the other. The first portion 12 is formed as a substantially flat member having an inner end 18, an outer front end 20, which is generally parallel to the end 18, and a pair of opposite sides 22 and 24. The first portion 12 can be formed in a trapezoidal shape, similar to the embodiment illustrated in FIG. 6 or other convenient shape having opposite front corners 26 and 28 spaced at sufficient distance as to be positioned immediately above the ingrown toenail corner, when the portion 12 is attached to top toenail surface 30 of toe 32. The upper surface 34 of the first portion 12 is formed smooth, while the inner surface 35 of the first portion 12 is provided with a locking plurality of parallel rows of tiny teeth 36 extending outwardly transversely from the complementary contactive bottom surface 35 or deposited thereon. The teeth 36 are inclined in their direction as can be better seen in FIG. 8, with the transversely projected teeth 36 angled inwardly, towards the end 18 of the portion 12, and when positioned on a toenail, are designed to be directed towards the root 38 of the toenail. The bottom surface 35 of the first portion 12 is also provided with an adhesive coating deposited on a bottom surface of the device along opposite sides 22 and 24, with the areas of application of the adhesive coating being designated by numerals 40 and 42 in FIG. 7 for attaching the device 10 to the top surface of the toenail.

As a result, the toothed surface is centrally located on the bottom surface 35 of the first portion 12 between the areas 40 and 42 of the bottom surface 35 which are covered with adhesive coating.

The second portion 14 of the device 10 is generally wedge-shaped and has a front end 44 and an inner end 46 which is integrally attached to one end of the intermediate portion 16. The second end of the intermediate portion 16 is integrally attached to the first portion 12 as illustrated in FIGS. 6 and 7. The top surface 48 of the portion 14, similarly to the surface 34 of the portion 12 is formed smooth, while the bottom surface 50 is provided with a plurality of parallel rows of tiny teeth 52 which match the teeth 36 of the portion 12. The teeth 52 are also angled in one direction, so that when the portion 14 is folded under the portion 12, as illustrated in step by step view of FIG. 8, the teeth 52 are positioned in an opposite direction from the teeth 36 and engage therewith, preventing a reverse movement of the wedge 14 from its engagement with the flat portion 12.

The portion 14 is also provided with one or more tooth-free surface areas 54, 56 for relieving pressure, and extending transversely to the general orientation of the tooth rows 52.

The intermediate portion 16 serves as a "buffer" absorbing at least some shocks imposed on the toenail 30 when the device 10 is in place. At the same time, the intermediate portion 16 serves to apply inward force in the direction of arrow 60 (see FIG. 8) when gradually wedging, in the course of time, the portion 14 between the bottom surface 35 of the portion 12 and the top surface of the toenail 30.

Figure 2:
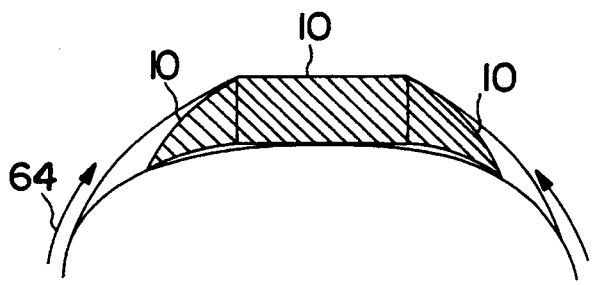
Figure 3:
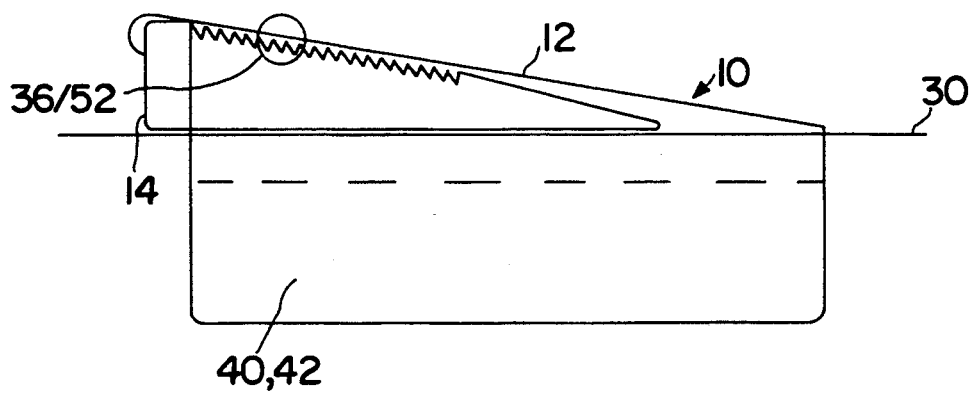
Figure 4:
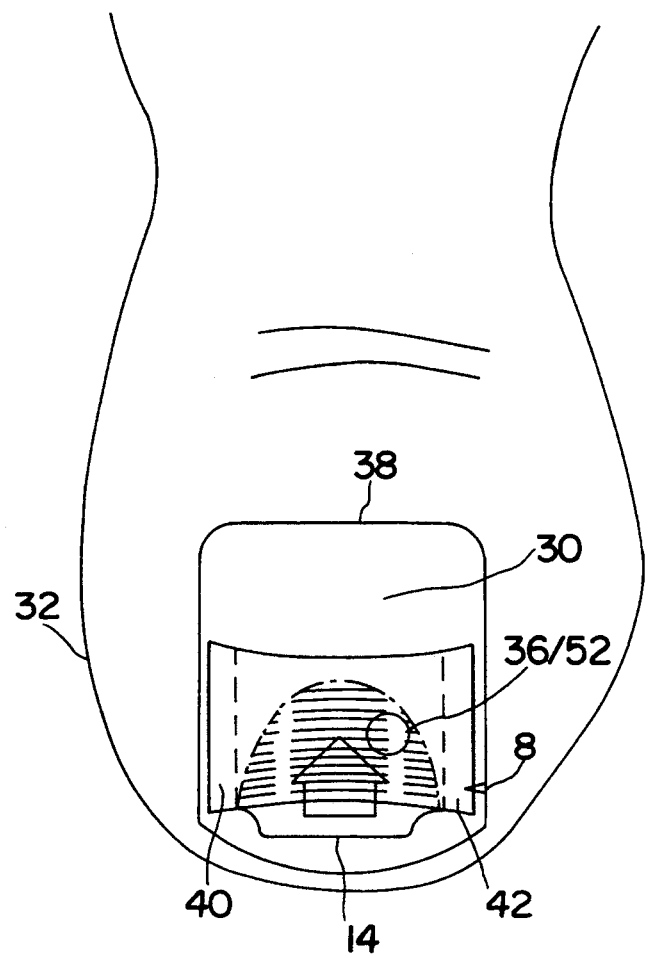
Figure 5:
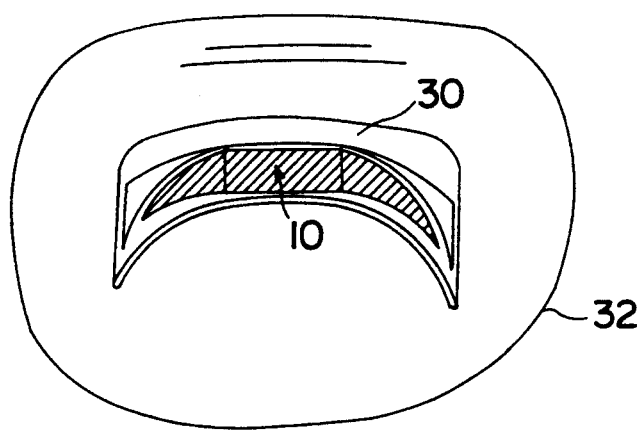

The device 10 is formed from a relatively flexible, non-resilient material, which allows the portion 12 to be slightly bent to conform to the convex top surface of the toenail 30, while being sufficiently strong to cause uplifting of ingrown corners 62 in the direction of arrows 64 (see FIG. 2) during use of the device.

I claim:

1. A device for reversing growth direction of ingrown toenail, comprising: a first, and a second plurality of locking means, said locking means adapted to intermate, and extend from complementary contactive surfaces of a first, and a second portion;

said first portion sized and shaped to generally correspond to a top surface of a human toenail, said first portion being provided with a means for attaching that first portion along opposite sides thereof to the toenail top surface, such that a forwardmost end of the first portion is positioned immediately adjacent to a toenail free end: and said second portion integrally connected to the first portion and being wedge-shaped to allow gradual insertion of the second portion between the first portion, secured to the toenail top surface, and that toenail top surface.

2. The device of claim 1, wherein said first portion and said second portion each have an upper surface and a bottom surface, and wherein a plurality of transverse rows of mating teeth are extending outwardly, transversely from the contactive bottom surfaces of the first portion, and the second portion, to allow securing of the second portion in a desired position in relation to the first portion, while intermeshing selected rows of mating teeth.

3. The device of claim 2, wherein said means for attaching the first portion comprises an adhesive coating deposited on the bottom surface of the first portion.

4. The device of claim 2, wherein said bottom surface of the second portion is provided with pressure relieving tooth-free surface extending perpendicularly to and between rows of teeth.

5. The device of claim 1, further comprises an intermediate portion, which is integrally connected to the first portion and the second portion, the intermediate portion allowing folding of the second portion under the first portion, while forming a buffer along a free edge of the toenail.

6. A device for reversing growth direction of an ingrown toenail, comprising:

a substantially flat first portion having general dimensions suitable for positioning on a top surface of an ingrown toenail, such that outer front corners of the first portion are positioned immediately adjacent ingrown toenail corners, when the first portion is attached to the toenail top surface, said first portion being provided with an adhesive coating deposited along opposite sides of a bottom surface of the first portion, and with a plurality of parallel rows of angled teeth extending outwardly transversely to the complementary contactive bottom surfaces of the first and second portions;

a reduced width substantially flat middle portion integrally connected to the outer end of the first portion; and a second portion having a wedge shape and integrally connected to a free end of the middle portion, said second portion being provided with a plurality of transverse rows of matching teeth extending in parallel relationship to the complementary rows of teeth of the first portion and angled in an opposite direction, said teeth of the second portion intermeshing with the teeth of the first portion when the second portion is folded under the first portion to apply a wedge-assisted lifting force on the toenail corners.

7. The device of claim 6, wherein said bottom surface of the second portion is provided with at least one pressure relieving tooth-free surface which extends perpendicularly to and between the rows of teeth.

8. A method for reversing growth direction of an ingrown toenail, comprising the following steps:

providing a device having a first portion sized and shaped to generally correspond to a top surface of a human toenail, said first portion having an upper surface and a bottom surface;

depositing adhesive coating along opposite sides of the bottom surface of the first portion;

providing a locking means of a plurality of parallel rows of angled teeth extending outwardly, transversely from the bottom surface of the first portion between the areas of adhesive coating;

providing an integrally connected second portion having a wedge shape and a complementary contactive bottom surface which is provided with a plurality of parallel rows of angled matching teeth;

folding the second portion under the first portion, causing intermeshing of matching teeth;

positioning the first portion on the toenail in such a manner that front opposite corners of the first portion are located above and immediately adjacent to corners of the ingrown toenail.

pressing the first portion to cause attachment of the first portion to the top surface of the toenail;

gradually forcing the second portion towards a root of a toenail, thereby gradually lifting corners of the ingrown toenail.

9. The method of claim 8, further comprising the step of providing an intermediate section having a generally smooth upper and bottom surfaces and integrally connected with the first portion and the second portion.

* * * * *